United States Patent [19]

Klötzer et al.

[11] Patent Number: 5,385,813
[45] Date of Patent: Jan. 31, 1995

[54] COLOR PHOTOGRAPHIC SILVER HALIDE MATERIAL

[75] Inventors: Sieghart Klötzer, Cologne; Otto Lapp, Bergisch Gladbach, both of Germany

[73] Assignee: Agfa-Gevaert AG, Leverkusen, Germany

[21] Appl. No.: 48,676

[22] Filed: Apr. 19, 1993

[30] Foreign Application Priority Data

Apr. 30, 1992 [DE] Germany .................. 4214196

[51] Int. Cl.$^6$ ............................... G03C 1/46
[52] U.S. Cl. ..................... 430/503; 430/554; 430/555; 430/558; 430/551; 430/607; 430/611
[58] Field of Search ............... 430/611, 558, 606, 554, 430/503, 551, 445, 555, 607

[56] References Cited

U.S. PATENT DOCUMENTS

| | | | |
|---|---|---|---|
| 3,305,362 | 2/1967 | Riester et al. | 96/66 |
| 4,657,847 | 4/1987 | Ikeda et al. | 430/445 |
| 4,886,738 | 12/1989 | Deguchi et al. | 430/611 |
| 5,037,733 | 8/1991 | Goda | 430/611 |
| 5,082,763 | 1/1992 | Kojima et al. | 430/611 |

FOREIGN PATENT DOCUMENTS 0369486  5/1990  European Pat. Off. .

*Primary Examiner*—Charles L. Bowers, Jr.
*Assistant Examiner*—Geraldine Letscher
*Attorney, Agent, or Firm*—Connolly and Hutz

[57] ABSTRACT

A color photographic silver halide material comprising at least one negatively developing, green-sensitive silver halide emulsion layer containing at least one magenta coupler can be adjusted to any desired sensitivity of that layer without any changes in other sensitometric properties by addition of at least one compound corresponding to general formula (I)

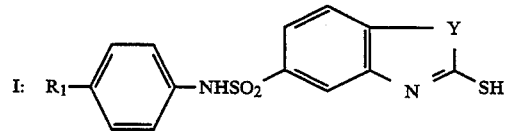

wherein
  is hydrogen or halogen,
  Y is NR$_2$, O or S and
  is hydrogen or C$_{1-4}$ alkyl.

3 Claims, No Drawings

COLOR PHOTOGRAPHIC SILVER HALIDE MATERIAL

This invention relates to a color photographic silver halide material comprising at least one negatively developing, green-sensitive silver halide emulsion layer containing at least one magenta coupler of which the sensitivity can be adjusted to exactly the required extent without significant changes in other sensitometric properties.

To obtain optimal results from a color photographic material, the individual silver halide emulsion layers containing color couplers have to be adapted to one another. To this end, the sensitivity of a spectrally sensitized silver halide emulsion layer often has to be reduced. This can be done by a number of measures, for example by reducing the average particle size, changing the particle size distribution, doping the silver halides with transition metals, such as iridium or rhodium, etc.

All these measures are limited in the extent to which they can be applied because the desired change in sensitivity is always accompanied by an unwanted change in another sensitometric property, particularly in the case of green-sensitive emulsions containing a magenta coupler. Thus, reciprocity errors occur in cases where the particle size is reduced while gradation is steepened in cases where the silver halides are doped with Ir or Rh.

The problem addressed by the present invention was to provide a method of finely controlling the sensitivity of a green-sensitive silver halide emulsion layer, in which these unwanted effects would be avoided or would at least be limited to a tolerable level.

It has now been found that the problem stated above can be solved by certain additions to the green-sensitized silver halide emulsion.

Accordingly, the present invention relates to a color photographic silver halide material of the type mentioned at the beginning, characterized in that the negatively developing green-sensitive silver halide emulsion layer contains at least one compound corresponding to general formula (I):

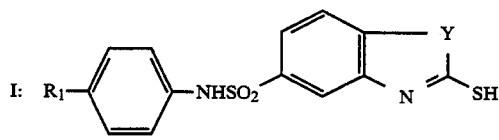

wherein
is hydrogen or halogen,
Y is $NR_2$, O or S and
is hydrogen or $C_{1-4}$ alkyl.

The compounds are known from U.S. Pat. No. 3,305,362.

The compound is added to the green-sensitized silver halide emulsion at any time before it is cast to form a silver halide emulsion layer, preferably after addition of the spectral sensitizer.

The compound is used in particular in quantities of 0.01 to 0.5 mmol/mol silver halide and preferably in quantities of 0.04 to 0.2 mmol/mol silver halide.

In addition to the at least one green-sensitive silver halide emulsion layer containing at least one magenta coupler, the color photographic material according to the invention preferably contains at least one red-sensitive silver halide emulsion layer containing at least one cyan coupler, at least one blue-sensitive silver halide emulsion layer containing at least one yellow coupler and typical interlayers and protective layers.

Binder, silver halide grains and color couplers are essential constituents of the photographic emulsion layers.

Gelatine is preferably used as binder although it may be completely or partly replaced by other synthetic, semisynthetic or even naturally occurring polymers. Synthetic gelatine substitutes are, for example, polyvinyl alcohol, poly-N-vinyl pyrrolidone, polyacrylamides, polyacrylic acid and derivatives thereof, particularly copolymers. Naturally occurring gelatine substitutes are, for example, other proteins, such as albumin or casein, cellulose, starch or alginates. Semisynthetic gelatine substitutes are generally modified natural products. Cellulose derivatives, such as hydroxyalkyl cellulose, carboxymethyl cellulose, and phthalyl cellulose and also gelatine derivatives which have been obtained by reaction with alkylating or acylating agents or by grafting on of polymerizable monomers are examples of such modified natural products.

The binders should contain an adequate number of functional groups, so that sufficiently resistant layers can be produced by reaction with suitable hardeners. Functional groups of the type in question are, in particular, amino groups and also carboxyl groups, hydroxyl groups and active methylene groups.

The gelatine preferably used may be obtained by acidic or alkaline digestion. Oxidized gelatine may also be used. The production of such gelatines is described, for example, in The Science and Technology of Gelatine, edited by A. G. Ward and A. Courts, Academic Press 1977, pages 295 et seq. The particular gelatine used should contain as few photographically active impurities as possible (inert gelatine). Gelatines of high viscosity and low swelling are particularly advantageous.

The silver halide present as photosensitive constituent in the photographic material is a silver bromide, bromide iodide, chloride bromide iodide, chloride bromide or chloride. Silver chloride bromides of high chloride content, for example at least 80 mol-% and preferably at least 95 mol-% are preferred.

The silver halide may consist of predominantly compact crystals which may have, for example, a regular cubic or octahedral form or transitional forms. However, the silver halide may also consist with advantage of platelet-like crystals of which the average diameter-to-thickness ratio is preferably at least 5:1, the diameter of a crystal being defined as the diameter of a circle with an area corresponding to the projected area of the crystal. However, the layers may also contain platy silver halide crystals in which the diameter-to-thickness ratio is considerably greater than 5:1, for example from 12:1 to 30:1.

The silver halide grains may also have a multiple-layer grain structure, in the most simple case with an inner and an outer core region (core/shell), the halide composition and/or other modifications such as, for example, doping of the individual grain regions, being different. The average grain size of the emulsions is preferably between 0.2 μm and 2.0 μm; the grain size distribution may be both homodisperse and heterodisperse. A homodisperse grain size distribution means that 95% of the grains differ from the average grain size by no more than ±30%. In addition to the silver halide, the emulsions may also contain organic silver salts, for example silver benztriazolate or silver behenate.

Two or more types of silver halide emulsions prepared separately may also be used in the form of a mixture.

The photographic emulsions may be prepared from soluble silver salts and soluble halides by various methods (cf. for example P. Glafkides, Chimie et Physique Photographique, Paul Montel, Paris (1967); G. F. Duffin, Photographic Emulsion Chemistry, The Focal Press, London (1966); V. L. Selikman et al., Making and Coating Photographic Emulsion, The Focal Press, London (1966)).

Precipitation of the silver halide is preferably carried out in the presence of the binder, for example gelatine, in the acidic, neutral or alkaline pH range, silver halide complexing agents preferably being additionally used. Silver halide complexing agents are, for example, ammonia, thioether, imidazole, ammonium thiocyanate or excess halide. The water-soluble silver salts and the halides are combined either successively by the single-jet process or simultaneously by the double-jet process or by any combination of both processes. The addition is preferably made at increasing inflow rates, although the "critical" feed rate at which new nuclei are still just not formed should not be exceeded. The pAg range may be varied within wide limits during precipitation. It is preferred to apply the so-called pAg-controlled method in which a certain pAg value is kept constant or the pAg value passes through a defined profile during precipitation. However, in addition to the preferred precipitation in the presence of an excess of halide, so-called inverse precipitation in the presence of an excess of silver ions is also possible. The silver halide crystals may be grown not only by precipitation, but also by physical ripening (Ostwald ripening) in the presence of excess halide and/or silver halide complexing agents. The emulsion grains may even be predominantly grown by Ostwald ripening, for which purpose a fine-grained, so-called Lippmann emulsion is preferably mixed with a less readily soluble emulsion and dissolved in and allowed to crystallize therefrom.

Salts or complexes of metals, such as Cd, Zn, Pb, Tl, Bi, Ir, Rh, Fe, Pt, Au, may be present during the precipitation and/or physical ripening of the silver halide grains. These metal compounds may be distributed in the grain either homogeneously or in phases (core, zone, shell).

In addition, precipitation may even be carried out in the presence of sensitizing dyes. Complexing agents and/or dyes may be inactivated at any time, for example by changing the pH value or by an oxidative treatment.

On completion of crystal formation or even at an earlier stage, the soluble salts are removed from the emulsion, for example by noodling and washing, by flocculation and washing, by ultrafiltration or by ion exchangers.

The silver halide emulsion is generally subjected to chemical sensitization under defined conditions (pH, pAg, temperature, gelatine, silver halide and sensitizer concentration) until sensitivity and fogging are both optimal. The process is described, for example, in H. Frieser "Die Grundlagen der Photographischen Prozesse mit Silberhalogeniden", pages 675–734, Akademische Verlagsgesellschaft (1968).

Chemical sensitization may be carried out with addition of compounds of sulfur, selenium, tellurium and/or compounds of the metals of the VIIIth secondary group of the periodic system (for example gold, platinum, palladium, iridium). Thiocyanate compounds, surface-active compounds, such as thioethers, heterocyclic nitrogen compounds (for example imidazoles, azaindenes) or even spectral sensitizers (described for example in F. Hamer "The Cyanine Dyes and Related Compounds", 1964, and in Ullmanns Encyclopädie der technischen Chemie, 4th Edition, Vol. 18, pages 431 et seq. and Research Disclosure No. 17643, Section III) may also be added. Reduction sensitization with addition of reducing agents (tin(II) salts, amines, hydrazine derivatives, aminoboranes, silanes, formamidine sulfinic acid) may be carried out instead of or in addition to chemical sensitization by hydrogen, by a low pAg value (for example below 5) and/or a high pH value (for example above 8).

In addition to the compounds according to the invention, suitable compounds of this type are azaindenes, preferably tetra- and pentaazaindenes, particularly those substituted by hydroxyl or amino groups. Compounds such as these are described, for example, by Birr, Z. Wiss. Phot. 47 (1952) pages 2 to 58. Other suitable antifogging agents are salts of metals, such as mercury or cadmium, aromatic sulfonic acids or sulfinic acids, such as benzenesulfinic acid, or nitrogen-containing heterocycles, such as nitrobenzimidazole, nitroindazole, optionally substituted benztriazoles or benzthiazolium salts.

The stabilizers may be added to the silver halide emulsions before, during or after ripening. The compounds may of course also be added to other photographic layers associated with a silver halide layer.

The photographic emulsion layers or other hydrophilic colloid layers of the photosensitive material produced in accordance with the invention may contain surface-active agents for various purposes, such as coating aids, for preventing electrical charging, for improving surface slip, for emulsifying the dispersion, for preventing adhesion and for improving the photographic characteristics (for example development acceleration, high contrast, sensitization, etc.). In addition to natural surface-active compounds, for example saponin, synthetic surface-active compounds (surfactants) are mainly used: nonionic surfactants, for example alkylene oxide compounds, glycerol compounds or glycidol compounds; cationic surfactants, for example higher alkylamines, quaternary ammonium salts, pyridine compounds and other heterocyclic compounds, sulfonium compounds or phosphonium compounds; anionic surfactants containing an acid group, for example a carboxylic acid, sulfonic acid, phosphoric acid, sulfuric acid ester or phosphoric acid ester group; ampholytic surfactants, for example amino acid and aminosulfonic acid compounds and also sulfur or phosphoric acid esters of an aminoalcohol.

The photographic emulsions may be spectrally sensitized using methine dyes or other dyes. Particularly suitable dyes are cyanine dyes, merocyanine dyes and complex merocyanine dyes.

A review of the polymethine dyes suitable as spectral sensitizers, suitable combinations thereof and supersensitizing combinations thereof can be found in Research Disclosure 17643/1978, Section IV.

The following dyes (in order of spectral regions) are particularly suitable:

1. as red sensitizers
    9-ethylcarbocyanines with benzthiazole, benzselenoazole or naphthothiazole as basic terminal groups, which may be substituted in the 5- and/or 6-position by halogen, methyl, methoxy, carbalkoxy, aryl, and also 9-ethyl naphthoxathia- or selenocarbocyanines and 9-ethyl naphthothiaoxa- and benzimidazocarbocyanines, providing the dye contains at least one sulfoalkyl group at the heterocyclic nitrogen;

2. as green sensitizers 9-ethylcarbocyanines with benzoxazole, naphthoxazole or a benzoxazole and a benzthiazole as basic terminal groups and also benzimidazocarbocyanines which may also be further substituted and must also contain at least one sulfoalkyl group at the heterocyclic nitrogen;

3. as blue sensitizers symmetrical or asymmetrical benzimidazo-, oxa-, thia- or selenacyanines containing at least one sulfoalkyl group at the heterocyclic nitrogen and, optionally, other substituents at the aromatic nucleus and also apomerocyanines containing a thiocyanine group.

There is no need for sensitizers where the natural sensitivity of the silver halide is sufficient for a certain spectral region, for example the blue sensitivity of silver bromide iodides.

Non-diffusing monomeric or polymeric color couplers are associated with the differently sensitized emulsion layers and may be arranged in the same layer or in an adjacent layer. Cyan couplers are normally associated with the red-sensitive layers, magenta couplers with the green-sensitive layers and yellow couplers with the blue-sensitive layers.

Color couplers for producing the cyan component dye image are generally couplers of the phenol or α-naphthol type.

Color couplers for producing the magenta component dye image are generally couplers of the 5-pyrazolone type, the indazolone type or the pyrazoloazole type, more particularly pyrazolotriazoles.

Color couplers for producing the yellow component dye image are generally couplers containing an openchain ketomethylene group, more especially couplers of the α-acyl acetamide type, of which suitable examples are α-benzoyl acetanilide couplers and α-pivaloyl acetanilide couplers.

The color couplers may be 4-equivalent couplers and also 2-equivalent couplers. 2-Equivalent couplers are derived from the 4-equivalent couplers in that they contain in the coupling position a substituent which is eliminated during the coupling reaction.

The couplers typically contain a ballast group to make diffusion within the material, i.e. both within a layer or from layer to layer, impossible. Couplers containing a ballast group may even be replaced by high molecular weight couplers.

High molecular weight couplers are described, for example, in DE-C-1 297 417, DE-A-24 07 569, DE-A-31 48 125, DE-A-32 17 200, DE-A-33 20 079, DE-A-33 24 932, DE-A-33 31 743, DE-A-33 40 376, EP-A-27 284, U.S. Pat. No. 4,080,211. The high molecular weight color couplers are generally produced by polymerization of ethylenically unsaturated monomeric color couplers. However, they may also be obtained by polyaddition or polycondensation.

The couplers or other compounds may be incorporated in silver halide emulsion layers by initially preparing a solution, a dispersion or an emulsion of the particular compound and then adding it to the casting solution for the particular layer. The choice of a suitable solvent or dispersant depends upon the particular solubility of the compound.

Methods for introducing compounds substantially insoluble in water by grinding processes are described, for example, in DE-A-26 09 741 and DE-A-26 09 742.

Hydrophobic compounds may also be introduced into the casting solution using high-boiling solvents, so-called oil formers. Corresponding methods are described, for example in US-A-2,322,027, US-A-2,801,170, US-A-2,801,171 and EP-A-0 043 037.

Instead of using high-boiling solvents, it is also possible to use oligomers or polymers, so-called polymeric oil formers.

The compounds may also be introduced into the casting solution in the form of charged latices, cf. for example DE-A-25 41 230, DE-A-25 41 274, DE-A-28 35 856, EP-A-0 014 921, EP-A-0 069 671, EP-A-0 130 115, US-A-4,291,113.

Anionic water-soluble compounds (for example dyes) may also be incorporated in non-diffusing form with the aid of cationic polymers, so-called mordant polymers.

Suitable oil formers are, for example, phthalic acid alkyl esters, phosphonic acid esters, phosphoric acid esters, citric acid esters, benzoic acid esters, amides, fatty acid esters, trimesic acid esters, alcohols, phenols, aniline derivatives and hydrocarbons.

Examples of suitable oil formers are dibutyl phthalate, dicyclohexyl phthalate, di-2-ethyl hexyl phthalate, decyl phthalate, triphenyl phosphate, tricresyl phosphate, 2-ethyl hexyl diphenyl phosphate, tricyclohexyl phosphate, tri-2-ethyl hexyl phosphate, tridecyl phosphate, tributoxyethyl phosphate, trichloropropyl phosphate, di-2-ethyl hexyl phenyl phosphate, 2-ethyl hexyl benzoate, dodecyl benzoate, 2-ethyl hexyl-p-hydroxybenzoate, diethyl dodecaneamide, N-tetradecyl pyrrolidone, isostearyl alcohol, 2,4-di-tert.-amylphenol, dioctyl acetate, glycerol tributyrate, isostearyl lactate, trioctyl citrate, N,N-dibutyl-2-butoxy-5-tert.-octyl aniline, paraffin, dodecylbenzene and diisopropyl naphthalene.

The non-photosensitive interlayers generally arranged between layers of different spectral sensitivity may contain agents to prevent unwanted diffusion of developer oxidation products from one photosensitive layer into another photosensitive layer with different spectral sensitization.

Suitable agents of the type in question, which are also known as scavengers or DOP trappers, are described in Research Disclosure 17 643 (December 1978), Chapter VII, 17 842/1979, pages 94–97 and 18 716/1979, page 650 and in EP-A-69 070, 98 072, 124 877, 125 522 and in US-A-463,226.

Where several partial layers of the same spectral sensitization are present, they may differ from one another in regard to their composition, particularly so far as the type and quantity of silver halide crystals is concerned. In general, the partial layer of higher sensitivity is arranged further from the support than the partial layer of lower sensitivity. Partial layers of the same spectral sensitization may be arranged adjacent one another or may be separated by other layers, for example by layers of different spectral sensitization. For example, all the high-sensitivity layers and all the low-sensitivity layers may be respectively combined to form a layer unit or layer pack (DE-A-19 58 709, DE-A-25 30 645, DE-A-26 22 922).

The photographic material may also contain UV absorbers, whiteners, spacers, filter dyes, formalin scavengers, light stabilizers, antioxidants, $D_{min}$ dyes, additives for improving dye, coupler and white stabilization and for reducing color fogging, plasticizers (latices), biocides and other additives.

UV-absorbing compounds are intended on the one hand to protect image dyes against fading under the effect of UV-rich daylight and, on the other hand, as filter dyes to absorb the UV component of daylight on exposure and thus to improve the color reproduction of a film. Compounds of different structure are normally used for the two functions. Examples are aryl-substituted benzotriazole compounds (U.S. Pat. No. 3,533,794), 4-thiazolidone compounds (U.S. Pat. Nos. 3,314,794 and 3,352,681), benzophenone compounds (JP-A-784/71), cinnamic acid ester compounds (U.S. Pat. Nos. 3,705,805 and 3,707,375), butadiene compounds (U.S. Pat. No. 4,045,229) or benzoxazole compounds (U.S. Pat. No. 3,700,455).

It is also possible to use UV-absorbing couplers (such as cyan couplers of the α-naphthol type) and UV-absorbing polymers. These UV absorbers may be fixed in a special layer by mordanting.

Filter dyes suitable for visible light include oxonol dyes, hemioxonol dyes, styryl dyes, merocyanine dyes, cyanine dyes and azo dyes. Of these dyes, oxonol dyes, hemioxonol dyes and merocyanine dyes may be used with particular advantage.

Suitable whiteners are described, for example, in Research Disclosure 17 643 (December 1978), Chapter V, in U.S. Pat. No. 2,632,701 and 3,269,840 and in GB-A-852,075 and 1,319,763.

Certain binder layers, particularly the layer furthest from the support, but occasionally intermediate layers as well, particularly where they are the layer furthest from the support during production, may contain inorganic or organic, photographically inert particles, for example as matting agents or as spacers (DE-A-33 31 542, DE-A-34 24 893, Research Disclosure 17 643, December 1978, Chapter XVI).

The mean particle diameter of the spacers is particularly in the range from 0.2 to 10 μm. The spacers are insoluble in water and may be insoluble or soluble in alkalis, the alkali-soluble spacers generally being removed from the photographic material in the alkaline development bath. Examples of suitable polymers are polymethyl methacrylate, copolymers of acrylic acid and methyl methacrylate and also hydroxypropyl methyl cellulose hexahydrophthalate.

Additives for improving dye, coupler and white stability and for reducing color fogging (Research Disclosure 17 643/1978, Chapter VII) may belong to the following classes of chemical compounds: hydroquinones, 6-hydroxychromanes, 5-hydroxycoumaranes, spirochromanes, spiroindanes, p-alkoxyphenols, sterically hindered phenols, gallic acid derivatives, methylenedioxybenzenes, aminophenols, sterically hindered amines, derivatives containing esterified or etherified phenolic hydroxyl groups, metal complexes.

Compounds containing both a sterically hindered amine partial structure and also a sterically hindered phenol partial structure in one and the same molecule (U.S. Pat. No. 4,268,593) are particularly effective for preventing the impairment (deterioration or degradation) of yellow dye images as a result of the generation of heat, moisture and light. Spiroindanes (JP-A-159 644/81) and chromanes substituted by hydroquinone diethers or monoethers (JP-A-89 83 5/80) are particularly effective for preventing the impairment (deterioration or degradation) of magenta-red dye images, particularly their impairment (deterioration or degradation) as a result of the effect of light.

The layers of the photographic material may be hardened with the usual hardeners. Suitable hardeners are, for example, formaldehyde, glutaraldehyde and similar aldehyde compounds, diacetyl, cyclopentadione and similar ketone compounds, bis-(2-chloroethylurea),2-hydroxy-4,6-dichloro-1,3,5-triazine and other compounds containing reactive halogen (U.S. Pat. No. 3,288,775, U.S. Pat. No. 2,732,303, GB-A-974,723 and GB-A-l,167,207), divinylsulfone compounds, 5-acetyl-1,3-diacryloyl hexahydro-1,3,5-triazine and other compounds containing a reactive olefin bond (U.S. Pat. No. 3,635,718, U.S. Pat. No. 3,232,763 and GB-A-994,869); N-hydroxymethyl phthalimide and other N-methylol compounds (U.S. Pat. No. 2,732,316 and U.S. Pat. No. 2,586,168); isocyanates (U.S. Pat. No. 3,103,437); aziridine compounds (U.S. Pat. No. 3,017,280 and U.S. Pat. No. 2,983,611); acid derivatives (U.S. Pat. No. 2,725,294 and U.S. Pat. No. 2,725,295); compounds of the carbodiimide type (U.S. Pat. No. 3,100,704); carbamoyl pyridinium salts (DE-A-22 25 230 and DE-A-24 39 551); carbamoyloxy pyridinium compounds (DE-A-24 08 814); compounds containing a phosphorus-halogen bond (JP-A-113 929/83); N-carbonyloximide compounds (JP-A-43353/81); N-sulfonyloximido compounds (U.S. Pat. No. 4,111,926), dihydroquinoline compounds (U.S. Pat. No. 4,013,468), 2-sulfonyloxy pyridinium salts (JP-A-110 762/81), formamidinium salts (EP-A-0 162 308), compounds containing two or more N-acyloximino groups (U.S. Pat. No. 4,052,373), epoxy compounds (U.S. Pat. No. 3,091,537), compounds of the isoxazole type (U.S. Pat. No. 3,321,313 and U.S. Pat. No. 3,543,292); halocarboxaldehydes, such as mucochloric acid; dioxane derivatives, such as dihydroxydioxane and dichlorodioxane; and inorganic hardeners, such as chrome alum and zirconium sulfate.

Hardening may be carried out in known manner by adding the hardener to the casting solution for the layer to be hardened or by overcoating the layer to be hardened with a layer containing a diffusible hardener.

Among the classes mentioned, there are slow-acting and fast-acting hardeners and also so-called instant hardeners which are particularly advantageous. Instant hardeners are understood to be compounds which crosslink suitable binders in such a way that, immediately after casting but at the latest 24 hours and, preferably 8 hours after casting, hardening has advanced to such an extent that there is no further change in the sensitometry and swelling of the layer combination as a result of the crosslinking reaction. By swelling is meant the difference between the wet layer thickness and dry layer thickness during aqueous processing of the film (Photogr. Sci. Eng. 8 (1964), 275; Photogr. Sci. Eng. (1972), 449).

These hardeners which react very quickly with gelatine are, for example, carbamoyl pyridinium salts which are capable of reacting with free carboxyl groups of the gelatine so that these groups react with free amino groups of the gelatine with formation of peptide bonds and crosslinking of the gelatine.

There are diffusible hardeners which have the same hardening effect on all the layers of a layer combination. However, there are also non-diffusing, low molecular weight and high molecular weight hardeners of which the effect is confined to certain layers. With hardeners of this type, individual layers, for example the protective layer, may be crosslinked particularly highly. This is important where the silver halide layer is minimally hardened to increase the covering power of the silver and the mechanical properties have to be improved through the protective layer (EP-A 0 114 699).

The color photographic materials according to the invention are normally processed by development, bleaching, fixing and washing or by development, bleaching, fixing and stabilization without subsequent washing; bleaching and fixing may be combined into a single process step. Suitable color developer compounds are any developer compounds which are capable of reacting in the form of their oxidation product with color couplers to form azomethine or indophenol dyes. Suitable color developer compounds are aromatic compounds containing at least one primary amino group of the p-phenylenediamine type, for example N,N-dialkyl-p-phenylenediamines, such as N,N-diethyl-p-phenylenediamine, 1-(N-ethyl-N-methanesulfonamidoethyl)-3-methyl-p-phenylenediamine, 1-(N-ethyl-N-hydroxyethyl)-3-methyl-p-phenylenediamine and 1-(N-ethyl-N-methoxyethyl)-3-methyl-p-phenylenediamine. Other useful color developers are described, for example, in J. Amer. Chem. Soc. 73, 3106 (1951) and in G. Haist, Modern Photographic Processing, 1979, John Wiley and Sons, New York, pages 545 et seq.

Color development may be followed by an acidic stop bath or by washing.

The material is normally bleached and fixed immediately after color development. Suitable bleaches are, for example, Fe(III) salts and Fe(III) complex salts, such as ferricyanides, dichromates, water-soluble cobalt complexes. Particularly preferred bleaches are iron(III) complexes of aminopolycarboxylic acids, more especially for example ethylenediamine tetraacetic acid, propylenediamine tetraactic acid, diethylenetriamine pentaacetic acid, nitrilotriacetic acid, iminodiacetic acid, N-hydroxyethyl ethylene diamine triacetic acid, alkyliminodicarboxylic acids, and of corresponding phosphonic acids. Other suitable bleaches are persulfates and peroxides, for example hydrogen peroxide.

The bleaching/fixing bath or fixing bath is generally followed by washing which is carried out in countercurrent or consists of several tanks with their own water supply.

Favorable results can be obtained where a following finishing bath containing little or no formaldehyde is used.

However, washing may be completely replaced by a stabilizing bath which is normally operated in countercurrent. Where formaldehyde is added, this stabilizing bath also performs the function of a finishing bath.

EXAMPLES

A color photographic recording material was produced by application of the following layers in the order shown to a paper coated on both sides with polyethylene. The quantities shown are all based on 1 m². For the silver halide applied, the corresponding quantities of AgNO$_3$ are shown.

Example 1

Layer combination 1

1st layer (substrate layer) 0.2 g gelatine

2nd layer (blue-sensitive layer) blue-sensitive silver halide emulsion (99.5 mol-% chloride, 0.5 mol-% bromide, mean particle diameter 0.78 μm) of 0.50 g AgNO$_3$ containing 1.38 g gelatine 0.60 g yellow coupler Y-1 0.48 g tricresyl phosphate (TCP)

3rd layer (interlayer) 1.18 g gelatine 0.08 g 2,5-dioctyl hydroquinone 0.08 g dibutyl phthalate (DBP)

4th layer (green-sensitive layer) green-sensitized silver halide emulsion (99.5 mol-% chloride, 0.5 mol-% bromide, mean particle diameter 0.45 μm) of 0.40 g AgNO$_3$ containing 1.02 g gelatine 0.37 g magenta coupler M-1 0.40 g DBP 5th layer (interlayer) 1.20 g gelatine 0.66 g UV absorber corresponding to the formula

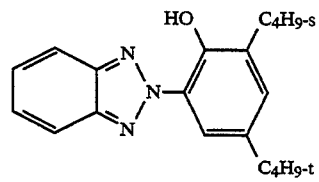

0.052 g 2,5-dioctyl hydroquinone 0.36 g TCP

6th layer (red-sensitive layer) red-sensitized silver halide emulsion (99.5 mol-% chloride, 0.5 mol-% bromide, mean particle diameter 0.42 μm) of 0.28 g AgNO$_3$ containing 0.84 g gelatine 0.39 g cyan coupler C-1 0.39 g TCP 7th layer (UV-absorbing layer) 0.65 g gelatine 0.21 g UB absorber as in the 5th layer 0.11 g TCP 8th layer (protective layer) 0.65 g gelatine 0.39 g' hardener corresponding to the following formula

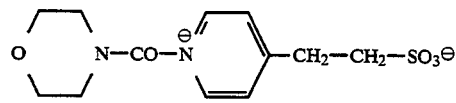

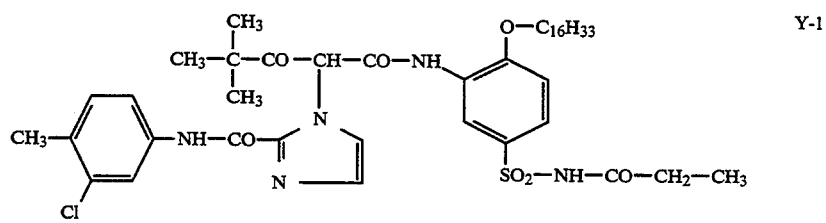

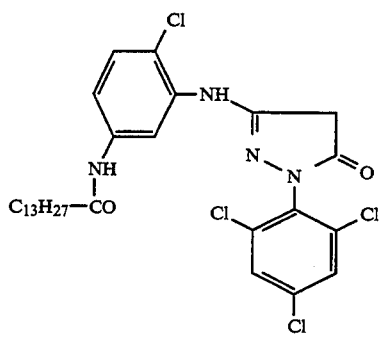

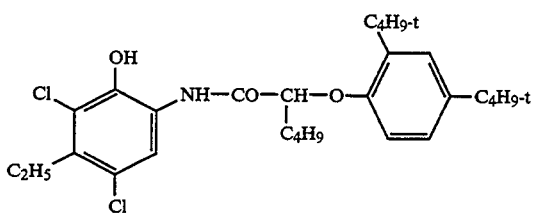

Processing

| a) Color developer - 45 s - 35° C. | |
|---|---|
| Triethanolamine | 9.0 g/l |
| N,N-diethyl hydroxylamine | 4.0 g/l |
| Diethylene glycol | 0.05 g/l |
| 3-Methyl-4-amino-N-ethyl-N-methane sulfonamidoethyl aniline sulfate | 5.0 g/l |
| Potassium sulfite | 0.2 g/l |
| Triethylene glycol | 0.05 g/l |
| Potassium carbonate | 22 g/l |
| Potassium hyroxide | 0.4 g/l |
| Ethylenediamine tetraacetic acid disodium salt | 2.2 g/l |
| Potassium chloride | 2.5 g/l |
| 1,2-Dihydroxybenzene-3,4,6-tri-sulfonic acid trisodium salt | 0.3 g/l |
| Make up with water to 1,000 ml; pH 10.0. | |
| b) Bleaching/fixing bath - 45 s - 35° C. | |
| Ammonium thiosulfate | 75 g/l |
| Sodium hydrogen sulfite | 13.5 g/l |
| Ammonium acetate | 2.0 g/l |
| Ethylenediamine tetraacetic acid (iron ammonium salt) | 57 g/l |
| Ammonia, 25% by weight | 9.5 g/l |
| Acetic acid | 9.0 g/l |
| Make up with water to 1,000 ml; pH 5.5 | |

The results in regard to fog (Dmin), sensitivity (log It) and gradation (gamma 1 and gamma 2) of this Example and of Examples 2 to 5 are set out in Table 1 below. It can be seen that compound 1 reduces sensitivity without affecting the other properties.

TABLE 1

| | Compound 1 | SENSITOMETRY | | | |
|---|---|---|---|---|---|
| Example | mg/mol Ag | Dmin | Log It | Gamma 1 | Gamma 2 |
| 1 | — | 0.080 | 1.79 | 2.11 | 3.75 |
| 2 | 13.6 | 0.078 | 1.74 | 2.14 | 3.69 |
| 3 | 27.2 | 0.079 | 1.71 | 2.09 | 3.72 |
| 4 | 40.8 | 0.078 | 1.68 | 2.12 | 3.70 |
| 5 | 51.0 | 0.077 | 1.65 | 2.10 | 3.73 |

Example 2

Layer combination as described in Example 1, except that the 4th layer (green-sensitive layer) additionally contains 0.032 g of compound 1. The material is processed in the same way as described in Example 1.

Example 3

Layer combination as described in Example 1, except that the 4th layer (green-sensitive layer) additionally contains 0,064 g of compound 1. The material is processed in the same way as described in Example 1.

Example 4

Layer combination as described in Example 1, except that the 4th layer (green-sensitive layer) additionally contains 0.096 g of compound 1. The material is processed in the same way as described in Example 1.

Example 5

Layer combination as described in Example 1, except that the 4th layer (green-sensitive layer) additionally contains 0.120 g of compound 1. The material is processed in the same way as described in Example 1.

Compound 1:

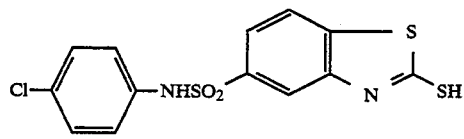

We claim:

1. A color photographic silver halide material comprising at least one negatively developing, green-sensitive silver halide emulsion layer containing at least one magenta coupler, characterized in that the green-sensitive silver halide emulsion layer contains at least one compound corresponding to general formula (I):

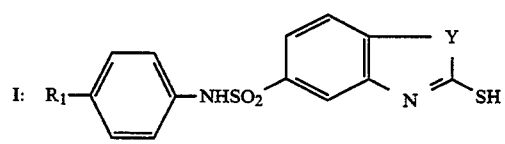

wherein is hydrogen or halogen,

Y is S.

2. A color photographic silver halide material as claimed in claim 1, characterized in that compound I is added in a quantity of 0.01 to 0.5 mmol/mol silver halide.

3. A color photographic silver halide material as claimed in claim 1, characterized in that at least 80 mol-% of the silver halide emulsion consists of silver chloride.

* * * * *

UNITED STATES PATENT AND TRADEMARK OFFICE
CERTIFICATE OF CORRECTION

PATENT NO. : 5,385,813
DATED : January 31, 1995
INVENTOR(S) : Klotzer et al

It is certified that error appears in the above-indentified patent and that said Letters Patent is hereby corrected as shown below:

On the cover page, in the Abstract section, third to last line, "is hydrogen or halogen," should read --$R_1$ is hydrogen or halogen,--.

In the last line of the Abstract section, "is hydrogen or $C_{1-4}$ alkyl." should read --$R_2$ is hydrogen or $C_{1-4}$ alkyl.--.

In column 13, line 2, "is hydrogen or halogen," should read --$R_1$ is hydrogen or halogen,--.

Signed and Sealed this

Fifth Day of September, 1995

*Attest:*

*Attesting Officer*

BRUCE LEHMAN

*Commissioner of Patents and Trademarks*